United States Patent
McNamara

(10) Patent No.: US 7,223,383 B2
(45) Date of Patent: May 29, 2007

(54) STABILIZED SUNSCREEN COMPOSITION HAVING A PARTICULATE INORGANIC SUNSCREEN

(75) Inventor: William E. McNamara, Middletown, NY (US)

(73) Assignee: Avon Products, Inc., New York, NY (US)

(*) Notice: Subject to any disclaimer, the term of this patent is extended or adjusted under 35 U.S.C. 154(b) by 357 days.

(21) Appl. No.: 10/744,482

(22) Filed: Dec. 23, 2003

(65) Prior Publication Data

US 2005/0136013 A1    Jun. 23, 2005

(51) Int. Cl.
*A61Q 17/04* (2006.01)
*A61Q 19/00* (2006.01)
*A61K 8/00* (2006.01)
*A61K 8/04* (2006.01)
*A61K 31/74* (2006.01)

(52) U.S. Cl. .................. 424/59; 424/60; 424/78.02; 424/78.08; 424/400; 424/401; 514/937

(58) Field of Classification Search .................. 424/59, 424/60, 78.02, 78.08, 400, 401; 514/937
See application file for complete search history.

(56) References Cited

U.S. PATENT DOCUMENTS 3,867,533 A * 2/1975 Schmolka .................. 514/311
6,464,965 B1 * 10/2002 Chiarelli et al. .............. 424/59
6,660,281 B1 * 12/2003 Nakanishi et al. .......... 424/401

* cited by examiner

*Primary Examiner*—Shelley A. Dodson
(74) *Attorney, Agent, or Firm*—Ohlandt, Greeley, Ruggiero & Perle, L.L.P.

(57) ABSTRACT

There is provided a composition. The cosmetic composition has the following: one or more particulates; a neutralized, carboxylic acid polymer selected from the group consisting of a carbomer, acrylates/$C_{10-30}$ alkyl acrylate crosspolymer, and any combination thereof; an amount of a polyoxyethylene/polyoxypropylene block copolymer effective to stabilize and maintain dispersion of the one or more particulates; and about 10 wt % to about 90 wt % water. There is also provided a method for making a sunscreen composition. There is also provided a method of stabilizing and maintaining dispersion of particulates in a cosmetic composition.

55 Claims, No Drawings

US 7,223,383 B2

STABILIZED SUNSCREEN COMPOSITION HAVING A PARTICULATE INORGANIC SUNSCREEN

BACKGROUND OF THE INVENTION

1. Field of the Invention

The present invention relates to a sunscreen composition having a particulate inorganic sunscreen stabilized and dispersed therein. The present invention further relates to a method for making a sunscreen composition in which a particulate inorganic sunscreen is stabilized and dispersed therein.

2. Description of the Related Art

Sunscreen compositions have commonly employed inorganic particulates, e.g., titanium dioxide and zinc oxide, in sunscreen agents. Such compositions have been formulated as anhydrous creams and lotions as well as aqueous emulsions. The most common form of emulsion employed is oil-in-water. Sunscreen emulsion compositions having inorganic sunscreen particulates are shown, for example, in U.S. Pat. Nos. 5,028,417; 5,188,831; 5,340,567; and 6,464,965.

One problem observed with sunscreen compositions having inorganic sunscreen particulates is they can feel heavy, oily, greasy and pasty in contact with the skin. Although oil-in-water emulsions exhibit these characteristics to a lesser degree than do water-in-oil emulsions or anhydrous creams and lotions, they nonetheless exhibit such characteristics.

Another problem observed with sunscreen compositions having inorganic sunscreen particulates is maintaining particulate dispersion and composition stability. One way employed in the prior art to improve dispersion and stability is to use particulates of very fine or relatively small sizes. Obtaining particulates of desired sizes may require use of complex grinding and/or milling processes.

Cosmetic compositions that employ organic and or inorganic pigments encounter many of the problems observed in sunscreen compositions. The term "pigment" refers to matter that imparts a phenomenon of light or visible perception that enables one to differentiate otherwise identical objects. Such pigments are typically supplied in particulate form like inorganic sunscreen particles. Compositions in which vibrant and rich color is desired require high levels of pigment, which can result in dispersion and agglomeration problems. Further, such compositions may not spread well. Pigment particulates are frequently treated or coated to reduce agglomeration and enhance dispersion and stability.

Carbomer gels have been employed in cosmetic and skin compositions because of their desirable aesthetic and feel properties. However, it has heretofore not been possible to use carbomer gels with a high loading of particulates due to dispersion and stability problems. The particulates have surface characteristics that can cause agglomeration and phase separation. Further, the gel breaks down and renders the composition nonfunctional as the pH of the gel changes over the course of time. Cosmetic and skin compositions having both a sunscreen and a carbomer are disclosed in U.S. Pat. Nos. 6,464,965; 6,491,930; and 6,521,217.

It would be desirable to have a composition having particulates that are stabilized and dispersed therein. It would also be desired to have such a composition in which the particulates are inorganic sunscreens and/or pigments. It would be further desired to have a composition with desirable aesthetic and feel characteristics on the skin. It would still be further desired to have a stabilized, dispersed carbomer gel composition having inorganic sunscreen and/or pigment particulates.

SUMMARY OF THE INVENTION

It is an object of the present invention to provide a composition having a particulate.

It is another object of the present invention to provide a stabilized, dispersed composition having a particulate.

It is still another object of the present invention to provide a composition having a particulate and that has desirable aesthetic and feel characteristics.

It is yet another object of the present invention to provide a stabilized, dispersed composition having a particulate and having the form of an emulsion, a water based gel, or an emulsion suspended within a water-based gel.

It is a further object of the present invention to provide a stabilized, dispersed composition having a particulate and having the form of a carbomer gel.

It is a still further object of the present invention to provide a stabilized, dispersed composition having a particulate in the form of an inorganic sunscreen and/or a pigment.

These and other objects and advantages of the present invention are achieved with the composition of the present invention. The cosmetic composition has the following: particulates; a neutralized, carboxylic acid polymer selected from the group consisting of a carbomer, acrylates/$C_{10-30}$ alkyl acrylate crosspolymer, and a combination thereof; an amount of a polyoxyethylene/polyoxypropylene block copolymer effective to stabilize and maintain dispersion of the particulates; and about 10 wt % to about 90 wt % water.

The present invention also provides a method for making a composition of the present invention. The method has the following steps: adding a carboxylic acid polymer to water and allowing it to hydrate; adding an amount of a basic compound effective to neutralize the carboxylic acid polymer; adding an amount of a polyoxyethylene/polyoxypropylene block copolymer effective to stabilize and maintain dispersion of particulates; and dispersing particulates therein. The carboxylic acid polymer is selected from the group consisting of a carbomer, acrylates/$C_{10-30}$ alkyl acrylate crosspolymer, and any combination thereof. The composition has about 10 wt % to about 90 wt % water.

The present invention also provides a method of stabilizing and maintaining dispersion of particulates in a cosmetic composition having a neutralized, carboxylic acid polymer selected from the group consisting of a carbomer, acrylates/$C_{10-30}$ alkyl acrylate crosspolymer, and any combination thereof; and about 10 wt % to about 90 wt % water. The method has the step of adding an effective amount of a polyoxyethylene/polyoxypropylene block copolymer.

DETAILED DESCRIPTION OF THE INVENTION

The present invention surprisingly found that a composition having a particulate could be formulated with desirable aesthetic and feel characteristics. It was also surprisingly found that a stabilized, dispersed composition could be formulated with a particulate of an inorganic sunscreen and/or a pigment including lakes.

The present composition has a carbomer and/or an acrylates/$C_{10-30}$ alkyl acrylate crosspolymer therein. Carbomers are homopolymers of acrylic acid crosslinked with an allyl ether of pentaerythritol, sucrose, or propylene. Acrylates/$C_{10-30}$ alkyl acrylate crosspolymers are copolymers of $C_{10-30}$ alkyl acrylates and one or more monomers of acrylic acid, methacrylic acid or their simple esters thereof crosslinked with an allyl ether of sucrose or pentaerythritol. The designation "$C_{10-30}$" refers to 10 to 30 carbon atoms. Carbomer is available from Noveon Incorporated under the tradename Carbopol. Examples of suitable carbomers include Carbopol 934, 934P, 940, 941, 954, 980, 981, 1342, 1382, 2984, and 5984; Aqua SF-1 polymer; and Carbopol ETD 2001 and ETD 2050; and Carbopol Ultrez 10. Carbomers are also available from the RITA Corporation under the tradename Acritamer. Carbopol 934, 940 and 941 are most preferred carbomers in the present invention. Acrylates/$C_{10-30}$ alkyl acrylate crosspolymers are also available from Noveon Incorporated under the tradename Pemulen TR1 or TR2, Carbopol 1342 or 1382, Carbopol ETD 2020, and Carbopol Ultrez 20 and 21. Additional description of carbomers is set forth in U.S. Pat. No. 6,464,965 B1, which description of carbomers is incorporated herein by reference.

The present composition is aqueous. Water is preferably present in an amount from about 10 weight percent (wt %) to about 90 wt %, more preferably in an amount from about 20 wt % to about 80 wt %, and most preferably in an amount from about 30 wt % to about 75 wt %, based on the total weight of the composition.

The particulate useful in the present composition may be any particulate known in the cosmetic and the topical/personal care art. The particulate may serve any function, including, but not limited to, coloring/pigmentation, UV absorption/reflection/blocking, body oil absorption/take-up, perspiration absorption/take-up, fragrancing/perfuming, insect repellency, fillers/vehicles, medicinal/pharmaceutical actives or carrier for same, appearance/aesthetics enhancing, feel enhancing, protection, film formation, exfoliation, conditioning, and cleansing. The particulate will be substantially insoluble in the composition or phase thereof. The particulate will be stabilized and dispersed within the composition.

The particulate in the present composition may be an inorganic sunscreen. Such inorganic sunscreens include, but are not limited to, titanium dioxide, zinc oxide and mica. A preferred inorganic sunscreen is titanium dioxide. The inorganic sunscreen is present in an amount effective to increase the SPF of the composition or reduce the amount of ultraviolet radiation reaching the skin. The inorganic sunscreen is preferably present in an amount from about 1 wt % to about 25 wt %, more preferably about 2 wt % to about 15 wt %, and most preferably about 5 wt % to about 10 wt %, based on the total weight of the composition. A preferred composition exhibits a SPF of about 10 to about 70. A most preferred composition exhibits a SPF of about 25 to about 50.

The particulate in the present composition may also be a pigment. The pigment may be one or more of the following: ochre, titanium dioxide, mica, titanated mica, kaolin, manganese-containing clay, iron oxide, nylon bead, and ceramic bead. The inorganic sunscreen is preferably present in an amount about 1 wt % to about 30 wt %, more preferably about 2 wt % to about 20 wt %, and most preferably about 5 wt % to about 15 wt %, based on the total weight of the composition.

The polyoxyethylene/polyoxypropylene block copolymer is employed in the present invention as a surfactant to maintain dispersion and stabilization of the particulate in the composition. The block copolymer helps prevent agglomeration and phase separation. The block copolymer is preferably a triblock copolymer. Both polyoxyethylene/polyoxypropylene/polyoxyethylene and polyoxypropylene/polyoxyethylene/polyoxypropylene triblocks are useful. The block copolymers are referred to in the art as pluronic surfactants. Useful block copolymers include Pluronic 31R1, 17R2, 17R4, 10R5, 25R2, L-43, L-61 and L-101 by BASF Corporation. The block copolymer is preferably present in an amount from about 1 wt % to about 25 wt %, more preferably about 3 wt % to about 20 wt %, and most preferably about 5 wt % to about 10 wt %, based on the total weight of the composition.

The basic compound is used in the method of the present invention to neutralize and stabilize the carbomer as well as to form a gel. Stabilizing the carbomer helps to stabilize the formed gel and substantially prevents the gel from collapsing, which can be initiated by the particulates. Useful basic compounds include, but are not limited to, organic amines such as aminomethyl propanol, ethanolamine, isopropanolamine and triethanolamine.

Another embodiment of the present invention is the method for making the composition. The carbomer is allowed to hydrate and is then neutralized with an amount of a basic compound sufficient to neutralize it. After neutralization, an effective amount of a polyoxyethylene/polyoxypropylene block copolymer is dispersed therein. An amount of a particulate inorganic sunscreen is then dispersed therein to form the composition. If desired, the method of making the composition may be carried out under normal processing conditions at ambient temperature and pressure and with conventional mixing techniques.

The composition may take the form of an emulsion, a water-based gel, or an emulsion suspended with a water-based gel. A preferred composition is a water-based gel. Useful emulsion forms include, but are not limited to, oil-in-water, water-in-oil, and triple emulsion. The composition may be formulated to exhibit a range of hardnesses and viscosities. The composition may be rigid, semi-rigid or fluidic. Preferably, the composition takes a semi-rigid or fluidic form such that it is pourable or squeezable and it can be readily dispensed from a rigid or squeezable container. The composition is applied to the surface of the skin and rubbed in.

The present composition may optionally contain vehicles other than water. Suitable hydrophilic vehicles include monohydric and polyhydric alcohols. Monohydric alcohols include those of 1 to 9 carbon atoms, such as ethanol, n-propanol, isopropanol, n-butanol and n-pentanol. Polyhydric alcohols include glycerin, ethylene glycol, propylene glycol, butylene glycol, pentylene glycol, hexylene glycol and oligomeric and polymeric forms of the foregoing. Other suitable hydrophilic vehicles include water-soluble silicones. Hydrophobic vehicles may also be employed in amounts such that phase separation does not occur and that the composition is not otherwise de-stabilized. Suitable hydrophobic vehicles include vegetable oils, fatty acid esters, fatty alcohols, mineral oils, silicone oils, hydrocarbon oils, and any combinations thereof. Sunscreen esters may also be used in the present invention, such as DEA-methoxycinnamate, octocrylene, and most preferably ethylhexylmethoxycinnamate.

The composition may optionally have non-particulate sunscreens. The sunscreens include, but are not limited to, p-aminobenzoic acid and salts and derivatives thereof (ethyl, isobutyl, and glyceryl esters; p-dimethylaminobenzoic acid; anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, octylmethoxy cinnamate, alpha-phenyl cinnamonitrile, and butyl cinnamoyl pyruvate); dihydroxycinnamic acid derivatives (umbelliferone, methylumbelliferone, and methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naptholsulfonates (sodium salts of 2-naphthol-3,6-disulfonic and of 2-naphthol-6,8-disulfonic acids); dihydroxy-naphthoic acid and salts thereof; o- and p-hydroxydiphenyldisulfonates; coumarin derivatives (7-hydroxy, 7-methyl, and 3-phenyl); diazoles (2-acetyl-3-bromoindazole, phenyl benzoxazole, methyl naphthoxazole, and various aryl benzothiazoles); quinine salts (bisulfate, sulfate, chloride, oleate, and tannate); quinoline derivatives (8-hydroxyquinoline salts and 2-phenylquinoline); hydroxy- or methoxy-substituted benzophenones; uric and vilouric acids; tannic acid and derivatives thereof; hydroquinone; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, octocrylene, and 4-isopropyl-dibenzoylmethane).

Optionally, the present compositions may include one or more of the following additional ingredients: botanical extracts, chelating agents, pigments, emollients, film formers, fragrances, humectants, lubricants, medicinal agents, moisturizers, preservatives, skin penetration enhancers, thickeners, vitamins and viscosity modifiers.

The following are examples of the present invention. Unless otherwise indicated, all parts and percentages are by weight.

EXAMPLES

Compositions can be prepared according to the present invention. The compositions are emulsions within a gel.

Example 1

| INGREDIENT | WEIGHT % |
| --- | --- |
| Demineralized Water | 74.04 |
| Carbopol 940 | 0.39 |
| Triethanolamine (99%) | 0.62 |
| Propylene Glycol | 2.33 |
| Methylparaben | 0.06 |
| Imidazolidinyl Urea | 0.06 |
| Ethylhexyl-Methoxycinnamate | 7.5 |
| Pluronic Block Polymer 31R1 | 10 |
| Titanium Dioxide (Eusolex T-S) | 5 |

Example 2

| INGREDIENT | WEIGHT % |
| --- | --- |
| Demineralized Water | 69.26 |
| Carbopol 940 | 0.36 |
| Triethanolamine (99%) | 0.58 |
| Propylene Glycol | 2.18 |
| Methylparaben | 0.06 |
| Imidazolidinyl Urea | 0.06 |
| Ethylhexyl-Methoxycinnamate | 7.50 |
| Pluronic Block Polymer 31R1 | 10 |
| Titanium Dioxide (Eusolex T-S) | 10 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A cosmetic composition, comprising:
   one or more particulates;
   a neutralized, carboxylic acid polymer selected from the group consisting of a carbomer, acrylates/$C_{10-30}$ alkyl acrylate crosspolymer, and any combination thereof;
   an effective amount of a polyoxyethylene/polyoxypropylene block copolymer; and
   about 10 wt % to about 90 wt % water.

2. The composition of claim 1, wherein the one or more particulates is an inorganic sunscreen.

3. The composition of claim 2, wherein the inorganic sunscreen is present in an amount about 2 wt % to about 15 wt % based on the total weight of the composition.

4. The composition of claim 2, wherein the inorganic sunscreen is present in an amount about 5 wt % to about 10 wt % based on the total weight of the composition.

5. The composition of claim 2, wherein the particulate inorganic sunscreen is selected from the group consisting of titanium dioxide, zinc oxide, mica, and any combinations thereof.

6. The composition of claim 2, wherein the inorganic sunscreen is titanium dioxide.

7. The composition of claim 1, wherein the one or more particulate is a pigment.

8. The composition of claim 1, wherein the carboxylic acid polymer is a carbomer.

9. The composition of claim 8, wherein the carbomer is present in an amount about 0.1 wt % to about 4 wt % based on the total weight of the composition.

10. The composition of claim 8, wherein the carbomer is present in an amount about 0.2 wt % to about 2 wt % based on the total weight of the composition.

11. The composition of claim 1, wherein the carboxylic acid polymer is an acrylates/$C_{10-30}$ alkyl acrylate crosspolymer.

12. The composition of claim 11, wherein the acrylates/$C_{10-30}$ alkyl acrylate crosspolymer is present in an amount about 0.1 wt % to about 4 wt % based on the total weight of the composition.

13. The composition of claim 11, wherein the acrylates/$C_{10-30}$ alkyl acrylate crosspolymer is present in an amount about 0.2 wt % to about 2 wt % based on the total weight of the composition.

14. The composition of claim 1, wherein the polyoxyethylene/polyoxypropylene block copolymer is present in an amount about 3 wt % to about 20 wt % based on the total weight of the composition.

15. The composition of claim 1, wherein the polyoxyethylene/polyoxypropylene block copolymer is present in an amount about 5 wt % to about 10 wt % based on the total weight of the composition.

16. The composition of claim 1, wherein the polyoxyethylene/polyoxypropylene block copolymer is a triblock copolymer.

17. The composition of claim 1, wherein the water is present in an amount about 20 wt % to about 80 wt % based on the total weight of the composition.

18. The composition of claim 1, wherein the water is present in an amount about 30 wt % to about 75 wt % based on the total weight of the composition.

19. The composition of claim 1, wherein the composition is a gel.

20. The composition of claim 1, wherein the composition is an emulsion.

21. The composition of claim 1, wherein the composition is an emulsion within a gel.

22. The composition of claim 1, wherein the one or more particulates is an inorganic sunscreen that is present in an amount about 2 wt % to about 15 wt %, wherein the carboxylic acid polymer is present in an amount about 0.1 wt % to about 4 wt %, wherein the polyoxyethylene/polyoxypropylene block copolymer is a triblock copolymer and is present in an amount about 3 wt % to about 20 wt %, and wherein the water is present in an amount about 20 wt % to about 80 wt %.

23. The composition of claim 22, wherein the composition is an emulsion within a gel.

24. A method for making a cosmetic composition:
a) adding a carboxylic acid polymer to water and allowing it to hydrate;
b) adding an amount of a basic compound effective to neutralize the carboxylic acid polymer;
c) adding an amount of a polyoxyethylene/polyoxypropylene block copolymer; and
d) dispersing particulates therein, wherein the polyoxyethylene/polyoxypropylene block copolymer is effective to stabilize and maintain dispersion of particulates, wherein the carboxylic acid polymer is selected from the group consisting of a carbomer, acrylates/$C_{10-30}$ alkyl acrylate crosspolymer, and any combination thereof, and wherein the composition has about 10 wt % to about 90 wt % water.

25. The method of claim 24, wherein the one or more particulates is an inorganic sunscreen.

26. The method of claim 25, wherein the inorganic sunscreen is present in an amount about 2 wt % to about 15 wt % based on the total weight of the composition.

27. The method of claim 25, wherein the inorganic sunscreen is present in an amount about 5 wt % to about 10 wt % based on the total weight of the composition.

28. The method of claim 25, wherein the inorganic sunscreen is selected from the group consisting of titanium dioxide, zinc oxide, mica, and any combinations thereof.

29. The method of claim 25, wherein the inorganic sunscreen is titanium dioxide.

30. The method of claim 24, wherein the one or more particulates is a pigment.

31. The method of claim 24, wherein the carboxylic acid polymer is a carbomer.

32. The method of claim 31, wherein the carbomer is present in an amount about 0.1 wt % to about 4 wt % based on the total weight of the composition.

33. The method of claim 31, wherein the carbomer is present in an amount about 0.2 wt % to about 2 wt % based on the total weight of the composition.

34. The method of claim 24, wherein the carboxylic acid polymer is an acrylates/$C_{10-30}$ alkyl acrylate crosspolymer.

35. The method of claim 34, wherein the acrylates/$C_{10-30}$ alkyl acrylate crosspolymer is present in an amount about 0.1 wt % to about 4 wt % based on the total weight of the composition.

36. The method of claim 34, wherein the acrylates/$C_{10-30}$ alkyl acrylate crosspolymer is present in an amount about 0.2 wt % to about 2 wt % based on the total weight of the composition.

37. The method of claim 24, wherein the polyoxyethylene/polyoxypropylene block copolymer is present in an amount about 3 wt % to about 20 wt % based on the total weight of the composition.

38. The method of claim 24, wherein the polyoxyethylene/polyoxypropylene block copolymer is present in an amount about 5 wt % to about 10 wt % based on the total weight of the composition.

39. The method of claim 24, wherein the polyoxyethylene/polyoxypropylene block copolymer is a triblock copolymer.

40. The method of claim 24, wherein the water is present in an amount about 20 wt % to about 80 wt % based on the total weight of the composition.

41. The method of claim 24, wherein the water is present in an amount about 30 wt % to about 75 wt % based on the total weight of the composition.

42. The method of claim 24, wherein the composition is a gel.

43. The method of claim 24, wherein the composition is an emulsion.

44. The method of claim 24, wherein the composition is an emulsion within a gel.

45. The method of claim 24, wherein the one or more particulates is an inorganic sunscreen and is present in an amount about 2 wt % to about 15 wt %, wherein the carboxylic acid polymer is present in an amount about 0.1 wt % to about 4 wt %, wherein the block copolymer is a triblock copolymer and is present in an amount about 3 wt % to about 20 wt %, and wherein the water is present in an amount about 20 wt % to about 80 wt %.

46. The method of claim 45, wherein the composition is an emulsion within a gel.

47. A method of stabilizing and maintaining dispersion of particulates in a cosmetic composition having a neutralized, carboxylic acid polymer selected from the group consisting of a carbomer, acrylates/$C_{10-30}$ alkyl acrylate crosspolymer, and any combination thereof, and about 10 wt % to about 90 wt % water, comprising adding an effective amount of a polyoxyethylene/polyoxypropylene block copolymer.

48. The composition of claim 1, wherein the one or more inorganic particulates are selected from the group consisting of titanium dioxide and mica.

49. The composition of claim 48, wherein the composition is a gel.

50. The composition of claim 22, wherein the one or more inorganic particulates are selected from the group consisting of titanium dioxide and mica.

51. The composition of claim 50, wherein the composition is a gel.

52. The method of claim 24, wherein the one or more inorganic particulates are selected from the group consisting of titanium dioxide and mica.

53. The method of claim 52, wherein the composition is a gel.

54. The method of claim 45, wherein the one or more inorganic particulates are selected from the group consisting of titanium dioxide and mica.

55. The method of claim 45, wherein the composition is a gel.

* * * * *